United States Patent [19]
Hanson et al.

[11] Patent Number: 5,317,273
[45] Date of Patent: May 31, 1994

[54] HEARING PROTECTION DEVICE EVALUATION APPARATUS

[75] Inventors: William J. Hanson, Bolton; Peter R. Teare, Westborough, both of Mass.

[73] Assignee: Liberty Mutual, Boston, Mass.

[21] Appl. No.: 964,778

[22] Filed: Oct. 22, 1992

[51] Int. Cl.$^5$ .............................................. H04R 29/00
[52] U.S. Cl. .................................... 324/616; 324/602; 73/646; 381/58
[58] Field of Search .............. 324/602, 603, 605, 606, 324/607, 608, 612, 613, 614, 616; 73/646, 647; 381/71, 183, 187, 188, 58

[56] References Cited

U.S. PATENT DOCUMENTS

| | | | |
|---|---|---|---|
| 2,891,217 | 6/1959 | Grieg et al. | 324/613 |
| 2,982,914 | 5/1961 | Stewart | 324/613 |
| 3,202,931 | 8/1965 | Koontz | 324/603 X |
| 3,217,247 | 11/1965 | Taber | 324/602 |
| 3,631,346 | 12/1971 | Riggs | 324/606 X |
| 3,729,598 | 4/1973 | Tegt et al. | 381/58 |
| 3,968,334 | 7/1976 | Padilla | 381/58 X |
| 4,020,298 | 4/1977 | Epley et al. | 73/599 |
| 4,060,701 | 11/1977 | Epley | 381/58 X |
| 4,061,041 | 12/1977 | Fletcher et al. | 73/646 |
| 4,124,818 | 11/1978 | Lin et al. | 324/614 X |
| 4,477,770 | 10/1984 | Tojo | 324/613 |
| 4,644,581 | 2/1987 | Sapiejewski | 381/183 X |

OTHER PUBLICATIONS

Effects of Cup, Cushion, Band Force, Foam Lining and Various Design Parameters on the Attenuation of Earmuffs, R. Paakkonen, Mar. 1991, vol. 38/No. 2, pp. 59–65.

Draft Standard, Working Group S12.10, Hearing Protector Attenuation Apr. 1992.

*Primary Examiner*—Kenneth A. Wieder
*Assistant Examiner*—Glenn W. Brown

[57] ABSTRACT

A portable hearing protection device evaluation apparatus which can be taken into the field to measure noise attenuation of a muff type hearing protection device under actual working conditions is provided. The apparatus includes two miniature microphones, one positioned inside a muff near the ear, the other positioned outside the muff to detect the noise in the environment. These two microphones simultaneously receive input signals which are provided to circuitry which determines and displays a single number output representing the noise attenuation.

18 Claims, 3 Drawing Sheets

HEARING PROTECTION DEVICE EVALUATION APPARATUS

BACKGROUND OF THE INVENTION

This invention relates to the testing of hearing protection devices.

Some industrial environments are very noisy due to hydraulic presses, grinding machines, and other industrial equipment. The noise from these machines can cause permanent hearing damage to employees if protection is not provided. Hearing conservation regulations, such as those promulgated by the Occupational Safety and Health Administration (OSHA), govern hearing protection for employees based on the number of decibels and the time of exposure. The decibel range is logarithmic from about 30 dB for virtually no sound, to about 130 dB for sound which is painful. An office, bank, or store might have a background noise level of about 40–55 dB, whereas a dance club might be about 100–120 dB.

To reduce the noise level in a high noise environment to an acceptable level, hearing protection devices (HPDs), such as muffs or ear plugs are used. HPDs are typically tested in a laboratory environment. According to one method, an artificial test head or dummy head, which has artificial flesh and artificial ear drums, is used. When testing a muff type protector, a microphone is positioned inside the head near the artificial ear drum and another microphone is positioned outside the muff. Typically, the noise attenuation test uses pink noise, an average of about 100 common industrial noises, as a noise source. The difference in sound levels received by the two microphones is calculated for each of a series of octaves or, sometimes, one third octaves. This difference is the attenuation of the HPD in each frequency range.

According to another method of testing, a person uses a muff or ear plugs, and noise is increased until he or she indicates that the noise is at a certain point, e.g., at the threshold of hearing. The person is separately tested with and without protection, and the two results are compared to determine the attenuation of the protection device.

These laboratory methods are not entirely adequate because they fail to consider what benefit people receive from the HPDs at an actual job site or factory. First, different industrial environments have much different noise patterns. A grinding machine and a hydraulic molding machine may have much different frequency characteristics. Some characteristics are regular and continuous, others are intermittent. Second, a muff is affected by various personal individual factors such as hair on the head, facial hair, eye glasses, and hard hats. Third, the wear and tear of the muff can affect how much noise is attenuated. Certain conditions of the muff vary as it ages, such as the wear of the lining, fatigue in the spring bands, and deterioration in the seals.

Accordingly, it is an object of the present invention to provide a hearing protection device evaluation apparatus which allows measurement in the field.

It is another object of the invention to provide a hearing protection device evaluation apparatus which is portable.

It is yet another object of the present invention to provide a hearing protection device evaluation apparatus which is easy to use by a test engineer.

It is still another object of the present invention to provide a hearing protection device evaluation apparatus which provides an easily readable and understandable indication of the noise attenuation.

SUMMARY OF THE INVENTION

In one aspect, the invention is a portable hearing protection device measuring apparatus which has two microphones, one for detecting noise outside a muff, the other for detecting noise inside the muff. The microphones detect noise simultaneously and each provides an input signal. Circuitry receives the input signal from each microphone and provides a single number output representing a difference between the noise detected by the two microphones. A display is provided which displays the single number output.

In preferred embodiments, the circuitry is enclosed by a hand held housing. The circuitry includes filters which filter the input signals according to an A weighted network, an amplifier for amplifying the input signal, a converter which receives the filtered signal and provides an output which represents the noise level received by the microphone, and comparison circuitry for comparing the detected noise of at least one of the microphones to a predetermined range and for providing an indication if the noise level is outside the range. The two microphones are miniature microphones, and the housing includes a battery powered power supply.

In another aspect, the invention features a portable hearing protection device measuring apparatus which has a first microphone for detecting noise on the outside of the muff, and a second miniature microphone for detecting noise at an ear inside the muff. Each microphone provides input signals to circuitry which receives the input signals and provides an output signal which represents noise attenuation of the muff. A hand held housing is provided which encloses the circuitry and which includes a user interface.

In preferred embodiments, the circuitry includes a filter which filters the input signals according to an A-weighted network, an amplifier, and a converter which receives the filtered output signal and provides an output which represents the noise level received by a microphone. The circuitry also includes comparison circuitry for determining whether the noise detected by at least one of the two microphones is within a predetermined range, and for providing an indication if the detected noise is outside the range.

In another aspect, the invention features a method for testing a muff type hearing protection device while it is worn by a person comprising the steps of positioning a first microphone inside a muff near an ear of the person, positioning a second microphone outside and on or near the muff, receiving signals from the microphones, and generating a single number output and displaying it on a display which is on a portable, hand held housing. The single number output represents the noise attenuation due to the muff.

The invention provides a portable evaluation apparatus which allows people to be tested under real life conditions. The apparatus can be used to ensure that the hearing protection device used by a person in a noisy environment sufficiently attenuates noise in that precise environment. Also, since muffs come in different sizes and styles, the evaluation apparatus can be used to compare the noise attenuation of different muffs under actual real life conditions. Even further, the evaluation apparatus can be used to test how well the muff fits on an employee. The apparatus can also be used to test over different cycles of operation in a work environment, e.g., the situation in which a source of noise is intermittent, as in the case of a hydraulic mold. Since the device tests real people under actual environmental conditions, it accounts for personal factors, such as hair style, facial hair, glasses, or hard hats. Furthermore, the testing takes into account how the muff is fitted, and whether its components have deteriorated with time.

DESCRIPTION OF THE PREFERRED EMBODIMENTS

Figure 1:
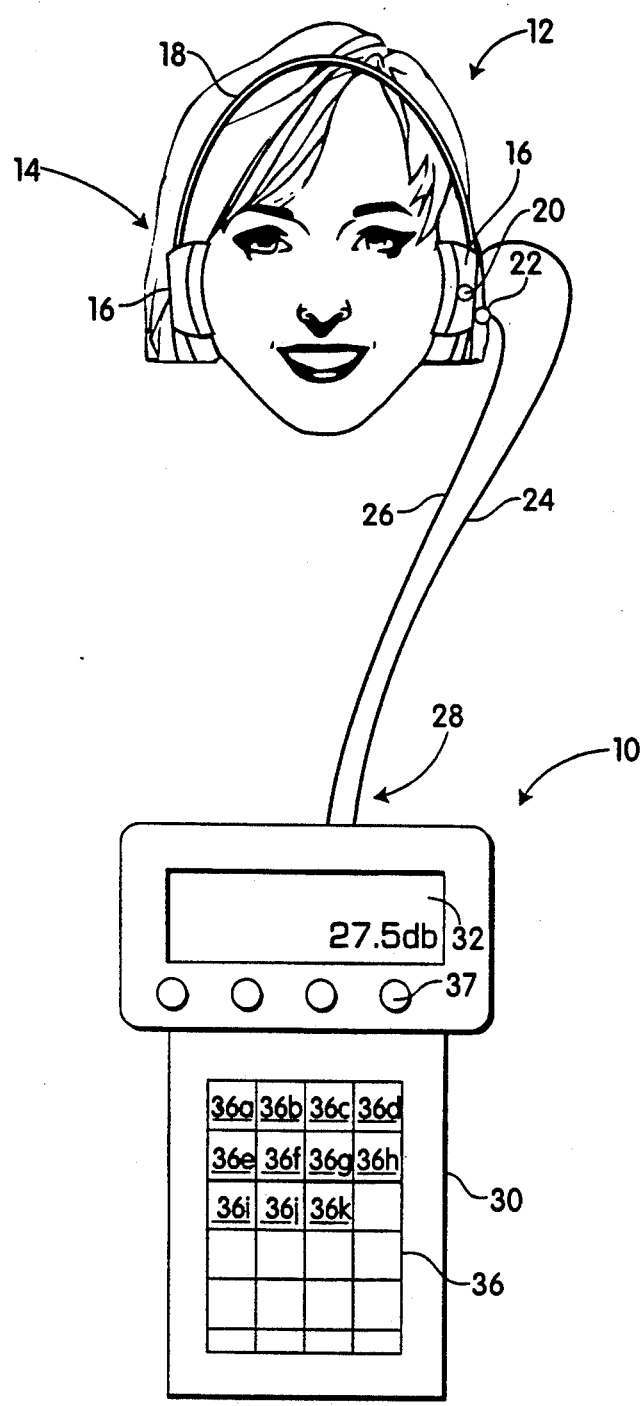
FIG. 1 is a front view of an embodiment of the present invention.

Referring to FIG. 1, a portable testing apparatus 10 is taken to a field location, such as a construction site or a factory, to test an individual 12 who is wearing a muff type hearing protection device (HPD) 14. The HPD 14 includes two muffs 16 and a spring band 18 for holding the HPD securely on the head. The testing apparatus 10 has an inside microphone 20 and an outside microphone 22 which are coupled by leads 24 and 26 to a port 28 on the testing apparatus 10. The inside microphone 20 is positioned on the end of a looped wire which wraps around a portion of the ear to hold the microphone securely near the ear. The ear and the inside microphone are covered by the muff 16. Outside microphone 22 is mounted to the outside of the muff 16 with double sided tape or by some other means for securely and removably mounting the microphone. The microphones are preferably miniature microphones, such as a BL 1785 model manufactured by Knowles, Inc. of Franklin Park, Ill. A miniature microphone has less effect on the measurement because the volume of the space enclosed between the ear and the muff is minimally changed with a small microphone.

The microphones provide an output level ranging from about 30 μV to 300 mV RMS, i.e., about an 80 dB range. When testing is performed, the employee is positioned so that the microphones are not in a "shadow zone" of the noise source, i.e. the noise is not coming from the other side of the employee's head. The microphones provide input signals over leads 24 and 26, which are thin shielded cables up to about 1.0 m long.

A housing 30 encloses circuitry which conditions signals from the leads 24 and 26, and provides a single number output on display 32. For example, a reading of 27.5 dB indicates that the muff provides a 27.5 dB attenuation, i.e., there is a 27.5 dB difference between the noise detected by the outside microphone 22 and the inside microphone 20. The housing 30 also has a keypad 36 and a warning light 37. The keypad 36 includes control keys, such as an on/off key 36a, a reset key 36b, a key 36c for controlling the type of output, a key 36d to operate the backlight, a key 36f to null channel one, a key 36g to null channel two, and keys 36h and 36i to undo the nulling of channels one and two, respectively.

Figure 2:
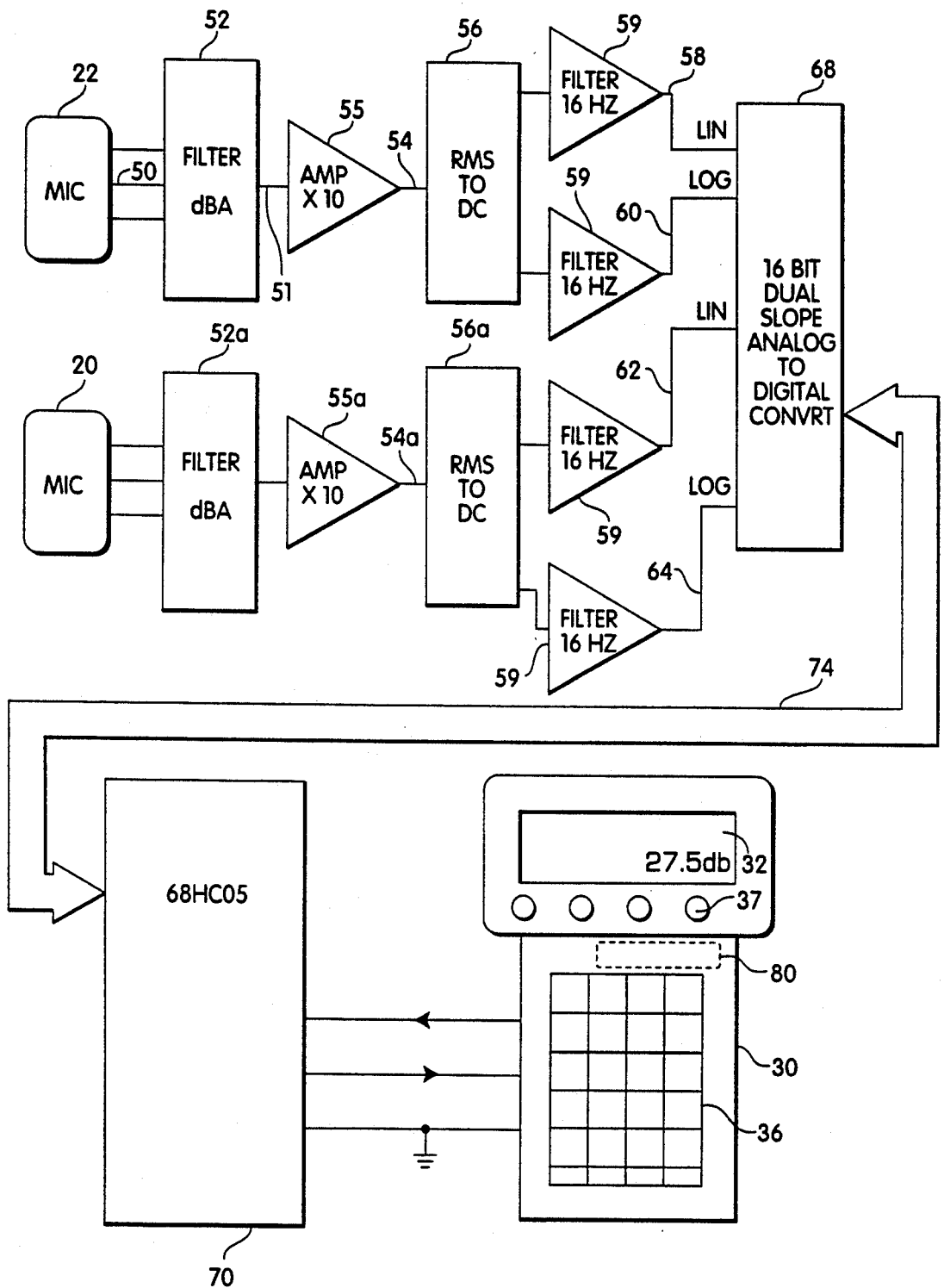
FIG. 2 is a block diagram of an embodiment of the present invention.
Figure 3:
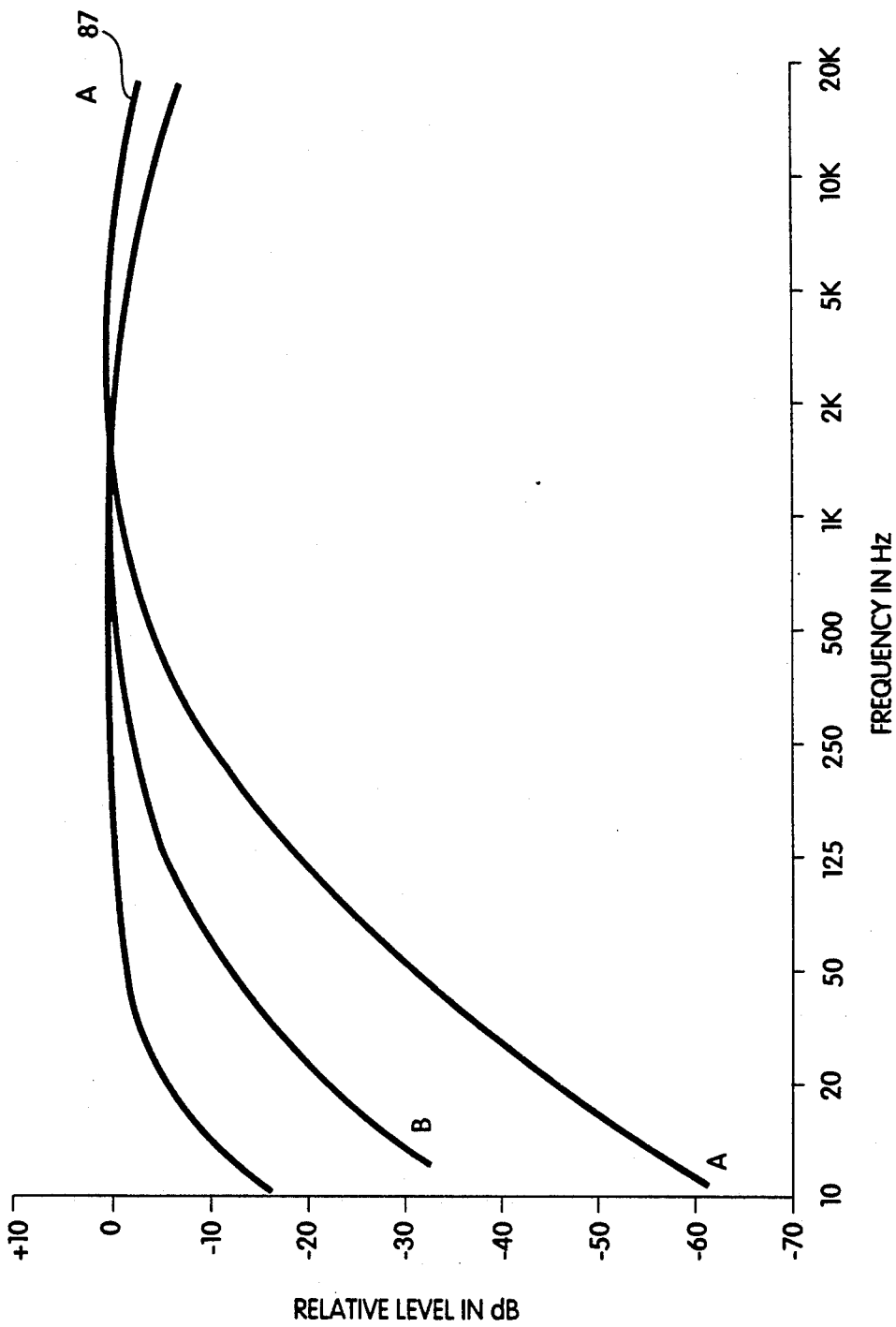
FIG. 3 is a graph of the frequency characteristics of an A weighted filter.

Referring to FIG. 2, the outside microphone 22 provides a signal 50 which is input to an A-weighted filter 52, which produces a filtered signal 51 according to an A weighted network. These A weights are designed to represent what a person actually hears. People can detect frequencies from about 20 Hz to about 20,000 Hz, but different ranges of frequencies are perceived differently. For example, at very low frequencies, people perceive less noise than what is detected at higher frequencies. The A-weighted filter 52 filters the signal to emulate human hearing. Referring to FIG. 3, a curve 87 shows the A weighted frequency characteristics in accordance with ANSI standards. The most significant difference is at low frequency, but there is little difference in the range from about 1000 Hz to 8000 Hz. Referring again to FIG. 2, the filtered signal 51 is amplified 20 dB by amplifier 55. Preferably the amplifier 55 is combined with the filter 52.

The output 54 of the amplifier 55 is provided to an Analog Devices AD636 RMS to DC converter 56. The converter provides two outputs which are filtered by filters 59, resulting in a linear output 58 and a logarithmic output 60. The linear output 58 provides 1.0 mV output for every 1.0 mV RMS input. The logarithmic output 60 provides a 3.0 mV output for every 1 dB of input by comparing the input voltage to a predetermined threshold amount to determine a relative number of decibels.

The inside microphone 20 similarly provides an input to a filter 52a. The filter 52a and amplifier 55a provide an output 54a which is an input to converter 56a. The converter provides a filtered linear output 62 and filtered logarithmic output 64. The filter 52a, amplifier 55a, and converter 56a are identical to the filter 52, the amplifier 55, and the converter 56, respectively.

The four outputs 58, 60, 62, and 64 are input signals to a sixteen bit analog-to digital converter 68 which is controlled by a microprocessor 70. The converter 68 preferably is a MAX 133, a dual slope, twenty reading per second, eight channel device which is manufactured by Maxim Integrated Products, Inc., of Sunnyvale, California. The twenty reading per second sample rate is divided by the number of channels being sampled. If the microprocessor only samples the two logarithmic outputs 60 and 64, the sample rate is ten readings per second. The filters 59 are selected at 16 Hz, greater than a sample rate of ten per second, to remove high frequency jitter.

The converter 68 receives the input signals and provides an output in terms of a number of counts. The converter should be capable of resolving a variation of at least about 20,000 counts since the desired resolution of counts per decibel preferably is about 290, and the desired range of the apparatus is at least 70 decibels. The MAX 133, for example, can accurately resolve 100,000 counts. Therefore, only a fraction of the range of the converter is used to cover the decibel range needed for the present invention. Since only the difference between the two channels is relevant, it is not crucial which portion of the 100,000 count range of the converter falls into the decibel range of the apparatus. In a typical application, the number of counts would range from about 50,000 for a detected noise level of about 60 dB to about 70,000 for a detected noise level of about 120 dB. The converter 68 successively provides five digits which represent the number of counts to the microprocessor 70 over bi-directional data lines 74.

The microprocessor, a Motorola 6805, determines which outputs to sample, reads the number of counts, calculates the absolute value of the difference between the counts of the two channels (e.g., outputs 60 and 64), and determines an output in terms of decibels by dividing the calculated absolute value number of counts by the number of counts per decibel. The microprocessor 70 causes this decibel value to be displayed on display 32. The absolute value step enables the microphones 20 and 22 to be interchangeable. The microprocessor performs these calculations and outputs the display value for each pair of count outputs from the converter, i.e. every one tenth second in the example described herein.

The microprocessor 70 checks the decibel values to ensure that they are within a range of 60–120 dB. If not, the warning light 37 is activated to indicate to the user that the detected noise level may be inaccurate. Typical noise attenuation due to a muff ranges from about 10–30 dB so the testing apparatus is designed to measure noise outside the muff in a range from about 80 dB and 120 dB. This restriction may limit application in a few instances, but provides the convenience of not having to set ranges.

Typically, a user will only want a reading in decibels, but a count output can be selected for field tests or for calibration by selecting the control button 36c (FIG. 1). When counts are selected, the number is provided without being divided and converted to decibels.

Prior to taking measurements, the testing apparatus may be calibrated with the keypad 36. In a quiet room, the microphones 20 and 22 are positioned adjacent one another or in contact with each other. A known calibrated noise source is placed over the microphones, and a reading is taken. The user adjusts the display with keys 36j and 36k (FIG. 1) on the keypad until the reading shows a zero decibel difference. Keys 36j and 36k internally adjust the offset in converters 56 or 56a, respectively. Small absolute errors are tolerable since the apparatus is primarily concerned with the difference in noise.

The housing 30 also encloses a battery pack and power supply 80 which provides +5 volts and −5 volts supply for the circuit elements. The battery power helps make the testing apparatus portable for measurements in the field.

While there has been shown and described what is at present considered the preferred embodiments of the present invention, it will be obvious to those skilled in the art that various changes and modifications may be made therein without departing from the scope of the invention as defined by the appended claims. For example, the apparatus could have four leads and four microphones, two for each muff.

What is claimed is:

1. A portable hearing protection device measuring apparatus for determining the noise attenuation of a muff type hearing protection device worn by a person in a noisy environment, said apparatus comprising:
    two microphones, one for detecting noise outside a muff, the other for detecting noise inside the muff, said microphones detecting noise received by each microphone simultaneously and providing input signals;
    circuitry for receiving the input signals and for providing an output including a single number output representing a difference between the noise detected by the two microphones; and
    a display for displaying the single number output.

2. An apparatus as set forth in claim 1 further comprising a hand held housing which encloses the circuitry.

3. An apparatus as set forth in claim 1 wherein for each microphone the circuitry includes:

a filter for receiving the input signal and for providing a filtered output signal; and
    a converter for receiving the filtered output signal and for providing a logarithmic output which represents the noise level detected by a microphone.

4. An apparatus as set forth in claim 3 wherein the circuitry further includes an amplifier for receiving the filtered output signal and for providing an amplified signal to the converter.

5. An apparatus as set forth in claim 3 wherein the filter includes an A-weighted filter.

6. An apparatus as set forth in claim 3 wherein the circuitry further includes an analog-to-digital converter which receives the logarithmic output and provides signal to a processor representing the logarithmic output.

7. An apparatus as set forth in claim 6 further comprising a hand-held housing which encloses the circuitry and a battery powdered power supply, wherein the microphones are miniature microphones, wherein one microphone is positioned inside a muff near an ear and one microphone is positioned outside and on or near the muff, and wherein the circuitry includes further comparison circuitry for determining whether the noise detected by at least one of the two microphones is within a predetermined range, and for providing an indication if the detected noise is outside the range.

8. An apparatus as set forth in claim 1 wherein one microphone is positioned inside the muff near the ear of the person, and one is positioned outside the muff.

9. An apparatus as set forth in claim 1 wherein the circuitry further comprises comparison circuitry for determining whether the noise detected by at least one of the two microphones is within a predetermined range, and for providing an indication if the detected noise is outside the range.

10. An apparatus as set forth in claim 1 wherein the microphones are miniature microphones.

11. A portable hearing protection device measuring apparatus for determining the noise attenuation of a muff-type hearing protection device while it is worn by a person in a noisy environment, said apparatus comprising:
    a first microphone for detecting noise on the outside a muff;
    a second microphone for detecting noise inside the muff near an ear of the person, said first microphone and said second microphone providing input signals which represent detected noise;
    circuitry for receiving the input signals and for providing an output signal representing noise attenuation of the muff; and
    a hand held housing for enclosing the circuitry, said housing including a user interface.

12. An apparatus as set forth in claim 11 wherein for each microphone the circuitry includes:
    a filter for receiving the input signal and for providing a filtered output signal; and
    a converter for receiving the filtered output signal and for providing a logarithmic output which represents the noise level of a microphone.

13. An apparatus as set forth in claim 12 wherein the filter includes an A weighted filter.

14. An apparatus as set forth in claim 12 wherein the circuitry includes an analog-to-digital converter which receives the logarithmic output and provides signals to a processor representing the logarithmic output.

15. An apparatus as set forth in claim 11 wherein the circuitry includes comparison circuitry for determining whether the noise detected by at least one of the two microphones is within a predetermined range, and for providing an indication if the detected noise is outside the range.

16. The apparatus of claim 11 wherein the second microphone is a miniature microphone.

17. A method for testing a muff-type healing protection device in a real environment in which a person would normally experience noise while the device is worn by the person, said method comprising the following steps:
   positioning a first microphone inside a muff, near an ear of the person;
   positioning a second microphone outside and on or near the muff, said second microphone for receiving noise in an environment in which the person would regularly experience noise;
   receiving signals from each of the first and second microphones;
   generating from the signals an output signal including a single number output which represents noise attenuation due to the muff; and
   displaying the single number output on a portable, hand-held user interface.

18. A portable hearing protection device measuring apparatus for determining the noise attenuation of a muff-type hearing protection device while it is worn by a person in a noisy environment, said apparatus comprising:
   a first microphone for detecting noise outside a muff;
   a second microphone for detecting noise inside the muff and near an ear of the person, said first microphone and said second microphone providing input signals which represent detected noise;
   circuitry for receiving the input signals and for providing an output signal representing noise attenuation due to the muff; and
   a portable user interface for receiving the output signal and for displaying sound attenuation information to a user.

* * * * *